United States Patent
Tucker et al.

(10) Patent No.: US 8,654,329 B2
(45) Date of Patent: Feb. 18, 2014

(54) PARALLEL MULTISENSOR OPTICAL PARTICLE SENSORS FOR FLOWING FLUID SYSTEMS

(71) Applicants: John E. Tucker, Centreville, VA (US); John F. Reintjes, Alexandria, VA (US)

(72) Inventors: John E. Tucker, Centreville, VA (US); John F. Reintjes, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/023,530

(22) Filed: Sep. 11, 2013

(65) Prior Publication Data

US 2014/0009621 A1  Jan. 9, 2014

Related U.S. Application Data

(63) Continuation-in-part of application No. 13/920,769, filed on Jun. 18, 2013, now Pat. No. 8,582,100.

(60) Provisional application No. 61/661,387, filed on Jun. 19, 2012, provisional application No. 61/785,541, filed on Mar. 14, 2013.

(51) Int. Cl.
*G01N 15/02* (2006.01)
*G01N 21/00* (2006.01)

(52) U.S. Cl.
USPC .................................. 356/335; 356/341

(58) Field of Classification Search
USPC .................................. 356/335–344
See application file for complete search history.

(56) References Cited

U.S. PATENT DOCUMENTS

| | | | | |
|---|---|---|---|---|
| 3,826,364 A * | 7/1974 | Bonner et al. | | 209/3.1 |
| 7,187,441 B1 * | 3/2007 | Sevick-Muraca et al. | | 356/336 |
| 7,990,525 B2 * | 8/2011 | Kanda | | 356/73 |
| 2003/0078703 A1 * | 4/2003 | Potts et al. | | 701/1 |
| 2008/0221711 A1 * | 9/2008 | Trainer | | 700/54 |
| 2011/0001963 A1 * | 1/2011 | Durack | | 356/301 |

\* cited by examiner

*Primary Examiner* — Gregory J Toatley
*Assistant Examiner* — Jarreas C Underwood
(74) *Attorney, Agent, or Firm* — US Naval Research Laboratory; Sally A. Ferrett

(57) ABSTRACT

An optical fluid monitoring system for imaging debris and other particles in a flowing fluid. The system can have multiple sensors (camera and viewing port) connected to a single, remotely located, laser and computer. The system can also include multiple lasers, viewing ports and cameras to be located at different locations in a flow, with each sensor being configured to image a different particle size range. The system can simultaneously image fluid flows on different pieces of equipment. Optical sensors can be arranged on parallel flow conduits, with each sensor configured to image a different particle size range.

25 Claims, 8 Drawing Sheets

PARALLEL MULTISENSOR OPTICAL PARTICLE SENSORS FOR FLOWING FLUID SYSTEMS

CROSS-REFERENCE TO RELATED APPLICATIONS

This application is a continuation-in-part of application Ser. No. 13/920,769 filed on Jun. 18, 2013. application Ser. No. 13/920,769 is a non-provisional of and claims the benefit of U.S. Provisional Application 61/661,387 filed on Jun. 19, 2012 and of U.S. Provisional Application 61/785,541 filed on Mar. 14, 2013. The entire disclosure of each of these documents is incorporated herein in its entirety.

BACKGROUND OF THE INVENTION

1. Technical Field

This is related to systems for optically monitoring objects suspended in flowing fluid, and more particularly, to particle monitoring systems for monitoring the presence and size of debris in oil.

2. Related Technology

U.S. Pat. No. 5,572,320 to Reintjes et al. and U.S. Pat. No. 6,049,381 disclose in-situ fluid samplers for identifying particles in a flowing fluid with an optical near-field imaging device. In this system, a single laser illuminator is co-located with a single viewing port and a single electronic camera, the camera output being analyzed for particulate content of the fluid with a single computer processor. U.S. Pat. No. 6,049,381 to Reintjes et al. discloses a real time suspended particle monitor that uses a pulsed collimated optical source to produce a series of images of particles in a flowing fluid. U.S. Pat. No. 7,921,739 to Fjerdingstad et al. discloses a real-time optical monitoring system having an automatic on line bottle sampling operation.

U.S. Pat. No. 8,056,400 to Reintjes et al. discloses a system for particle entrained fluid sampling in a high pressure or high flow rate fluid flow system.

Such sampling systems can identify the number, shape, and size of particles in fluids. Information about the metal or other particles present in lubricating fluid, for example, can provide valuable information about wear in the machinery or other system being lubricated.

BRIEF SUMMARY OF THE INVENTION

An optical fluid monitoring system for imaging particles in at least one conduit carrying a flowing fluid, includes a plurality of optical sensors positioned along the at least one conduit, each sensor positioned to transmit laser optical energy into a transparent viewing window in a fluid flow conduit in a direction across the direction of flow, each sensor having an optical imaging system for receiving the optical energy after it has passed through the fluid flow and for imaging particles in the fluid flow.

In one example, each optical sensor includes a laser. The lasers in each optical sensor can have different wavelengths. In some examples, each optical sensor includes at least one optical fiber configured to transmit the optical energy of the laser to the transparent viewing window. In some examples, the system includes a single laser that is operatively coupled to all of the optical sensors. In some examples, a plurality of optical fibers transmits the optical energy output of the laser to the transparent viewing windows.

In some examples, each imaging system includes a camera and a lens disposed between the camera and a viewing window in the conduit. In some examples, a plurality of sensors are arranged in series along a single conduit, wherein an upstream one of the plurality of sensors is configured to image a range of larger size particles and a downstream one of the plurality of sensors is configured to a range of smaller size particles, and for each sensor, the conduit thickness at that sensor is such that the particles in the size range to be imaged are in the optical near field of the imaging system, and wherein the upstream sensor conduit has a conduit thickness that is larger than the downstream sensor conduit. In some examples, at least one filter is positioned in the conduit sized to exclude particles larger than a predetermined size from reaching a downstream sensor.

In some examples, the plurality of sensors are arranged on parallel conduits, with a first of the plurality of sensors configured to image a range of larger size particles and a second of the plurality of sensors configured to image range of smaller size particles, and for each sensor, the conduit thickness at that sensor is such that the particles in the size range to be imaged are in the optical near field of the imaging system, and wherein the first sensor conduit has a conduit thickness that is larger than the second sensor conduit. The parallel conduits can connect to a main flow passage at a same tap point and at a same return point.

In some examples, the system also includes a single computer processor operatively connected to receive images from all of the imaging systems, the computer processor having programmed instructions for classifying particle shapes and sizes from the images received from the imaging system. The computer processor can be located remote from the optical sensors.

In some examples, each optical sensor includes a computer processor operatively connected to the imaging system in the optical sensor, with each of the computer processor having programmed instructions for classifying particle shapes and sizes from the images received from the imaging system.

In some examples, a single laser is operatively coupled to all of the optical sensors; and a single computer processor is operatively connected to receive images from all of the imaging systems, the computer processor having programmed instructions for classifying particle shapes and sizes from the images received from the imaging system.

In some examples, the optical fluid monitoring system is adapted for imaging particles in at least two different conduits carrying flowing fluids, the system having at least one of the optical sensors positioned along each of the different conduits to image the particles in the fluid in that conduit. The system can have at least two of the optical sensors positioned along each of the different conduits to image the particles in the fluid in that conduit. Each conduit can be part of a different piece of equipment.

DETAILED DESCRIPTION OF THE INVENTION

Figure 1:
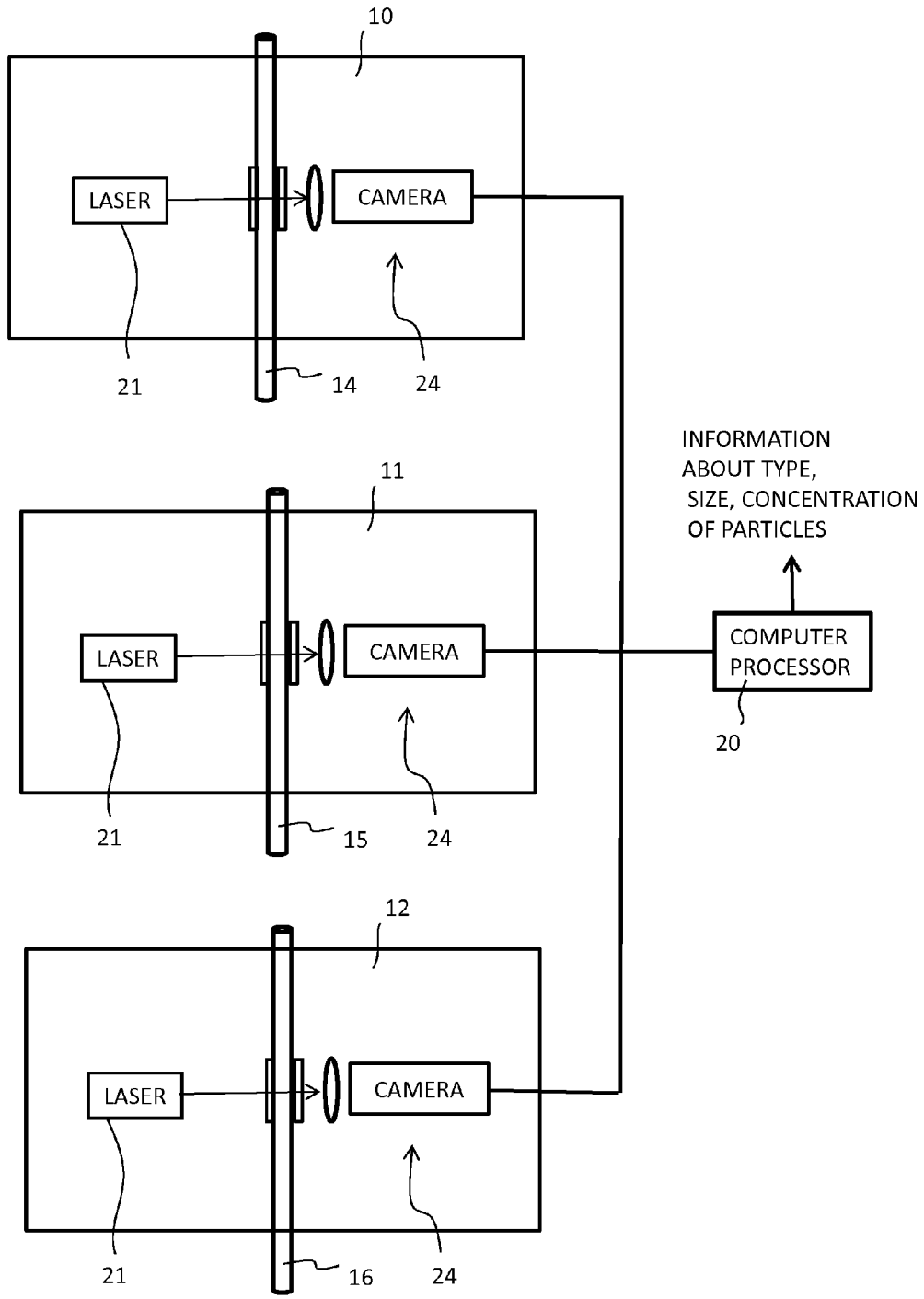
FIG. 1 illustrates an optical particle monitoring system for monitoring the fluid at several different locations.

FIG. 1 illustrates an optical particle monitoring system for fluids in accordance with an embodiment of the invention. The system includes a plurality of optical sensors or "sensor heads" 10, 11, 12, each configured to image the particles in a flowing fluid within a conduit 14, 15, 16. The fluid can be, but is not limited to, oil or another lubricant. The sensors can be located at different points along a single fluid flow, for example, at different locations along a conduit carrying coolant for a single aircraft engine. Alternatively, the sensors can be positioned to monitor different fluid flows in different components or devices. The sensor heads 10, 11, 12, can be remotely located at a distance from the operator's workstation and computer. In this example, each of the sensor heads includes a light source 21 such as a laser. The light travels through viewing windows in the conduit and is received by an imaging system 24.

Figure 2:
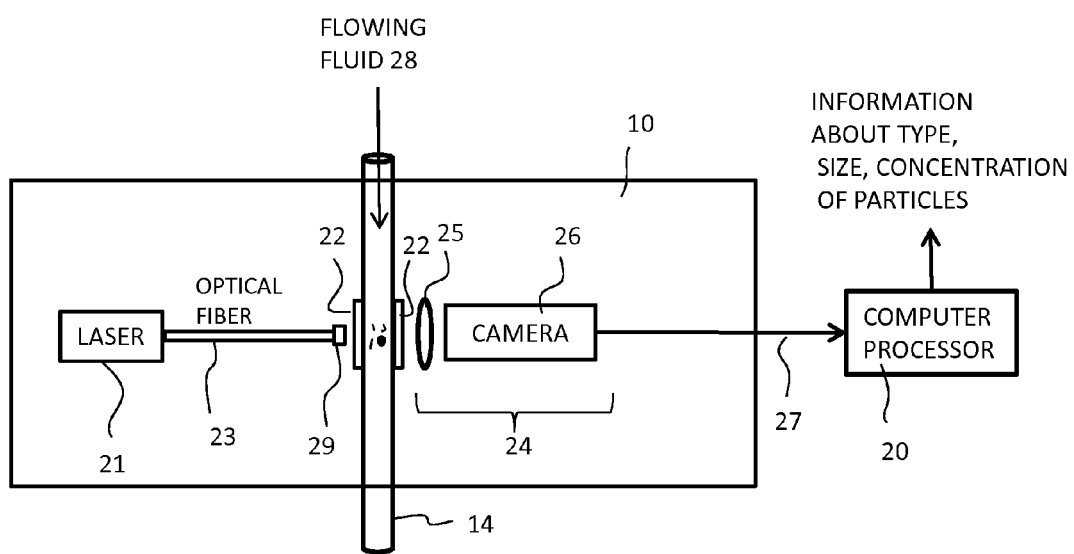
FIG. 2 illustrates an optical sensor head suitable for use in an optical particle monitoring system for fluid.

FIG. 2 illustrates a sensor head 10 suitable for use in an optical fluid particle monitoring system for fluids. Referring first to sensor head 10, the conduit 14 has an optically transparent portion 22 (a "viewing cell" or "windows") that allows light to be transmitted through the conduit. On one side of the conduit, optical energy from a light source 21 is directed through the window 22 into the flowing fluid 28. The viewing cell 22 is a channel with two windows on opposite sides of the channel that allow the light to pass through both windows, through the fluid, and out of the conduit to the imaging system 24.

The imaging system 24 is positioned on the other side of the viewing cell 22 to receive and image the portion of the optical energy that has passed through the flowing fluid. As particles in the fluid pass through the viewing cell, the light source 21 illuminates the particles, and the resulting shadows are detected by the imaging system 24. In this example, the light source 21 is a laser located near the viewing cell, with the laser light carried to the viewing window by an optical fiber 23.

In this example, the imaging system 24 can include an imaging lens 25 and an electronic camera 26, positioned so the lens focuses the image onto the camera's detector. The lens 25 can also enlarge the shadows to allow a desirable spatial resolution to be realized. The camera 26 transmits the images to a computer processor 20 for image analysis for identifying the number of particles, their size, and other information about the particles. Electronic image information is transmitted to the computer by cable 27, which can be either conductive or optical fiber, or by wireless signal transmission.

In an exemplary embodiment, the conduit is sized so that the particles at any position in the cell will be in the near field of the imaging system (the range appropriate for Fresnel diffraction), with constraints imposed by the particle size range, the wavelength of the light source, and the refractive index of the fluid.

The magnification of the imaging lens should be chosen to be appropriate for each size range and can be different for each viewing cell, in systems with more than one viewing cell.

A coherent light source is preferred, because while an incoherent light source could be used, a coherent light source allows the viewing cell thickness to be much larger than that allowed by an incoherent light source for the same particle size range.

The coherent light source wavelength can be selected such that a sufficient quantity of light is detectable, and enough light must also be absorbed or deflected by the particulate matter within the fluid such that there is a distinguishable difference between imaged portions of the fluid with particles and imaged portions of the fluid without particles. The wavelength of the light source can be selected to lie in a reasonably transparent region of the fluid. For oils and lubricants commonly encountered in mechanical machinery, such as aircraft or diesel engines, transmissions or gearboxes, a wavelength greater than 800 nm allows a sufficient quantity of light to be transmitted through the oil. A preferred wavelength range is between 800 and 1000 nm, but other wavelengths at which the fluid is transparent can be chosen. A single-mode diode laser with a wavelength of 830 nm can be used to illuminate the oil used in aircraft engines.

For other fluids that are transparent in other wavelength ranges, different wavelengths for the illumination laser can be chosen, commensurate with the requirements of transparency of the fluid and availability of suitable imaging detectors.

In operation, the light sources in the sensor head can be pulsed so a "stop action" image of fluid flowing within the chamber can be created. For each sensor head, with each pulse, a new image of fluid within the fluid chamber is created onto the optical detector. The pulse duration and the pulse repetition rate can be chosen with regard to the flow speed of fluid and optical transmission of the fluid. The duration of the pulse should be short enough so that during the pulse the particles do not move by more than the desired spatial resolution. The use of a short pulse duration with a two dimensional image allows reliable measures of particle size to be obtained without requiring knowledge or control of the flow speed.

The laser source can be a pulsed laser, or a continuous wave laser in combination with a laser modulator to generate optical pulses of coherent light. It can also be suitable to use a continuous wave laser without a modulator and to gate the images within the imaging system, if a camera with sufficiently fast gating is available.

Figure 3:
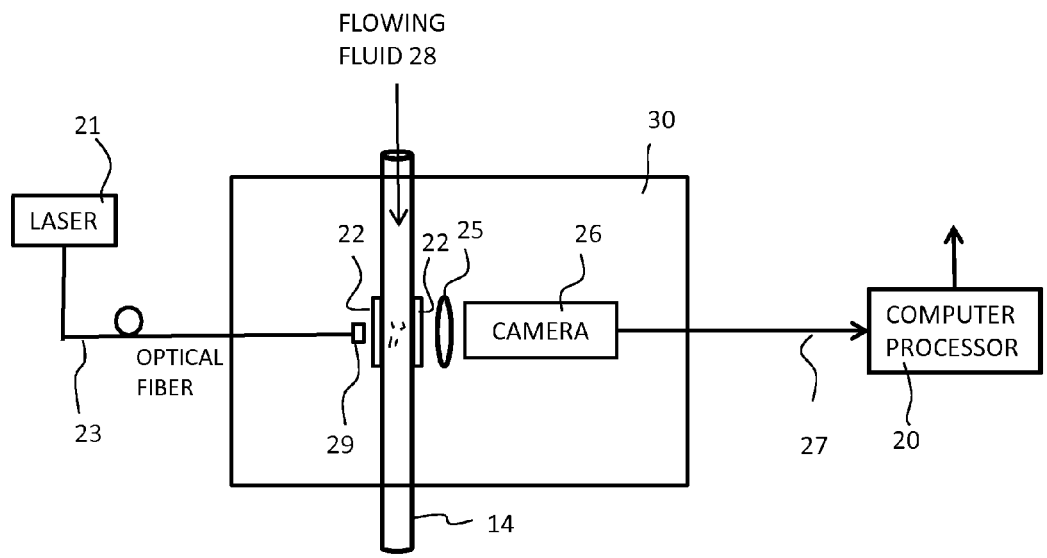
FIG. 3 shows an optical particle monitoring system for fluids in which the laser and computer processor are located remotely from the viewing window and conduit.
Figure 4:
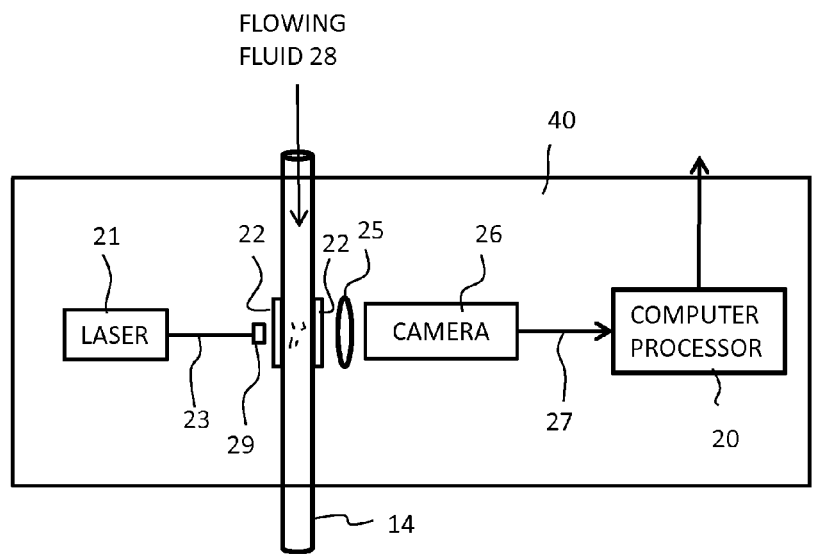
FIG. 4 shows an optical particle monitoring system for fluids in which the laser and computer processor are located close to the viewing window and conduit.

In the example shown in FIG. 2, the laser 21 is located close to the view cell 22. In another example shown in FIG. 3, the laser 21 is located remotely from the viewing cell and the optical fiber 23 carries the light to the viewing cell 22. The computer processor 20 is also located remotely from the viewing window and conduit. The sensor head 30 includes the end of the optical fiber 33, the viewing cell 22, and imaging system including a lens 25 and a camera 26. In FIG. 4, both the laser 21 and the computer processor 20 are located near the viewing window and conduit, as part of the sensor head 40.

In each example, a small beam expander 29 can be positioned at the end of the optical fiber near the viewing window to expand the beam to a size that is commensurate with the required resolution and the size of the camera before the light enters the viewing window.

Figure 5:
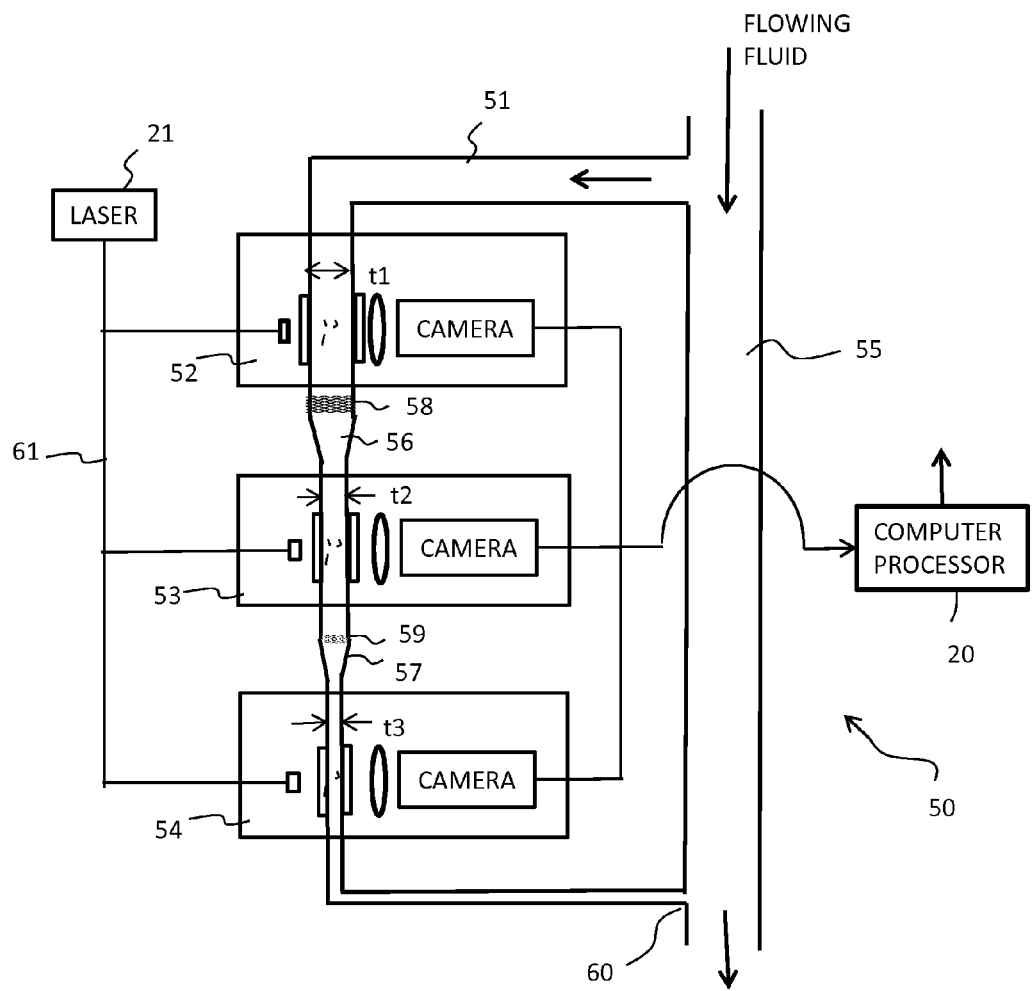
FIG. 5 illustrates an optical particle monitoring system with multiple sensor heads.

FIG. 5 illustrates a system that includes multiple sensor heads for evaluating the flow through a conduit, and for imaging particles over a larger range of sizes than could be imaged by a single sensor that uses near field optical imaging techniques. The combination of cell thicknesses can be chosen to be appropriate for each particle size range, with some overlap of particle size range from one cell to another, or the ranges can be disjoint, with no overlap between size ranges. It is preferable that the cells are arranged in order such that fluid flow encounters the largest viewing cell thickness first and then encounters progressively smaller cells. Screen mesh or other filters can be distributed between the cells to prevent larger particles from clogging the smaller cells. The ability to simultaneously monitor a fluid for particles of various sizes is very useful in monitoring the condition of mechanical systems, in which early wear is associated with smaller particles and more advanced wear is indicated by the presence of larger particles.

In this example, a single laser illuminator 21, with multiple optical fiber multiplexing, provides illumination to the sensor heads 52, 53, and 54. Optical fibers 61 are connected between the laser and the sensor heads and provide the light to the viewing cells in each sensor head. Alternatively, each sensor head can include a laser. The cameras in each sensor head transmit the images to a computer processor 20 for image processing and particle size analysis, although it is also suitable to include individual computer processors in each sensor head.

In this example, the thickness of the viewing cell in each sensor head is chosen to allow a particular range of particle sizes to be imaged, such that the objects throughout a cell are in the optical near field. The combination of cell thicknesses can be chosen to cover an overall range of particle sizes that is larger than that provided by a single cell. The sequence of cell thicknesses should be arranged such that the fluid flow encounters the largest cell first and then progressively smaller cells. Screen mesh filters can be distributed between the cells to prevent larger particles from clogging smaller cells.

In FIG. 5, the first sensor head 52 is the first one encountered by the fluid in the conduit 51. A filter 57 can be positioned upstream of the first sensor head to exclude particles above a size threshold. The conduit size can be reduced to ensure that the thickness t1 of the viewing window is the desired thickness to ensure particles of the size desired to be imaged are in the optical near field.

A second sensor head 53 is positioned downstream of the first sensor head. The second sensor head has a viewing cell with thickness t2<t1, that is suitable for imaging a range of particles with smaller sizes than the first sensor head, although there can be some overlap of particle ranges imaged by the first and second sensor heads. A pipe reducing fitting 56 is shown in the conduit between the sensor heads 52 and 53, to reduce the conduit diameter to the desired thickness t2 for the viewing window in the second sensor head 53.

A filter 58 can be positioned in the conduit between the first and second sensor heads to exclude undesirably large particles from entering the viewing window (e.g., particles that are large enough to clog the downstream viewing cells).

A third sensor head 54 is provided downstream of the sensor head 53. The sensor head 54 is configured to image particles of even smaller size than those imaged by the viewing cells in sensor head 53. A pipe reduction fitting 57 can be positioned between the upstream sensor head 53 and the downstream sensor head 54 to reduce the conduit size from the larger t2 thickness to a smaller t3 thickness to match the desired viewing cell thickness. A filter 59 can be included with a mesh size that excludes particles that are large enough to clog the viewing cell. It is noted that the mesh sizes of the filters can also be selected to limit the particle size to a maximum size that can be imaged by the downstream viewing windows. The flow in the conduit 51 can be returned to the main fluid flow 55 at a downstream location 60.

It is to be understood that the number of sensor heads can be greater or fewer than that shown in FIG. 5, depending on the complexity of the system to be monitored.

In an exemplary embodiment, the computer processor receives images from the sensor heads and performs image processing with a classifier module. The computer processor can determine, from the images, meaningful information about the population of particles in the fluid flow at each sensor head location. This information can include the number of particles in each particle size range and other quantities, such as but not limited to, concentrations of air bubbles, water bubbles, non metallic particles, fibers, wear particles (cutting, sliding fatigue) and biological entities.

Figure 6A:
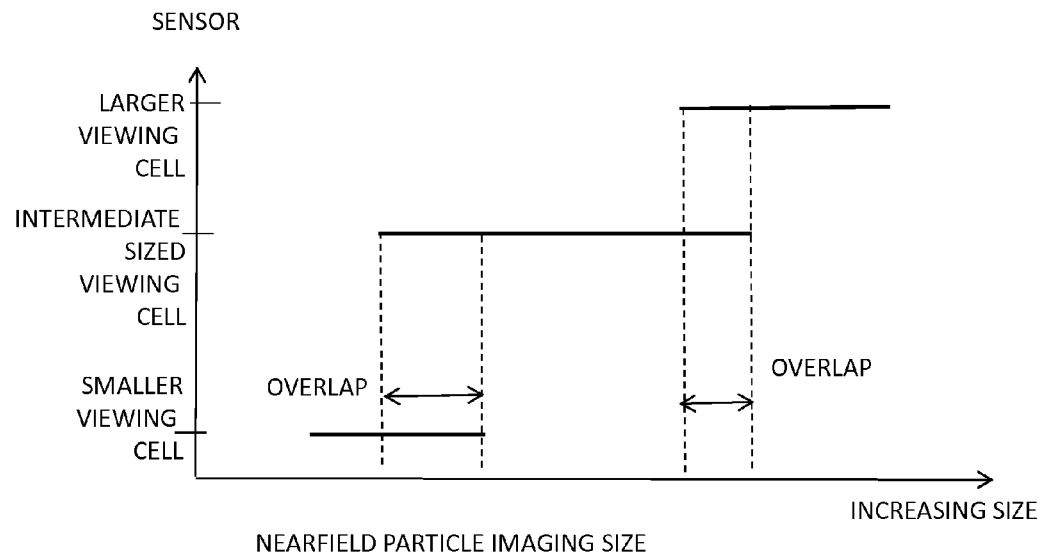
FIGS. 6A and 6B illustrate options for selecting viewing cell thicknesses to monitor different particle size ranges.
Figure 6B:
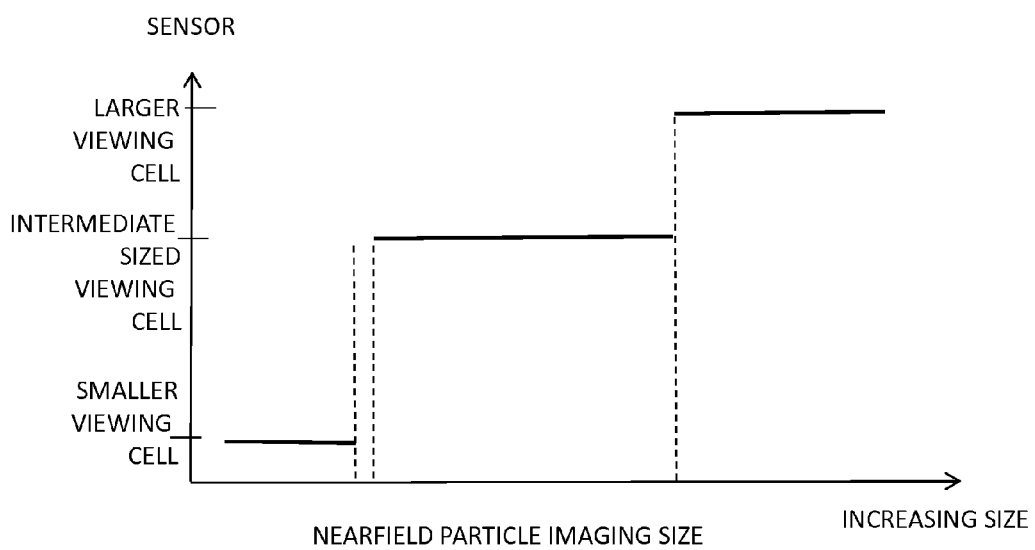

FIGS. 6A and 6B illustrate how possible combinations of cell thicknesses can be chosen to be appropriate for each particle size range. FIG. 6A shows the result of selecting cell thicknesses to ensure some overlap of particle size range from one cell to another. FIG. 6B shows the result of selecting cell thicknesses such that the particle size images are disjoint, with no overlap between imaged particle size ranges.

In an exemplary embodiment, the image processing system embodied in the computer processor 20 instructions can select particular size ranges which are of greater interest for each sensor head. The particle size ranges can be disjoint or can provide a chosen degree of overlap, which can be used to register the particle counting results from one cell to the next. It is noted that if the overall particle size range has disjoint ranges in individual cells, gaps in the monitored particle sizes can occur.

Figure 7:
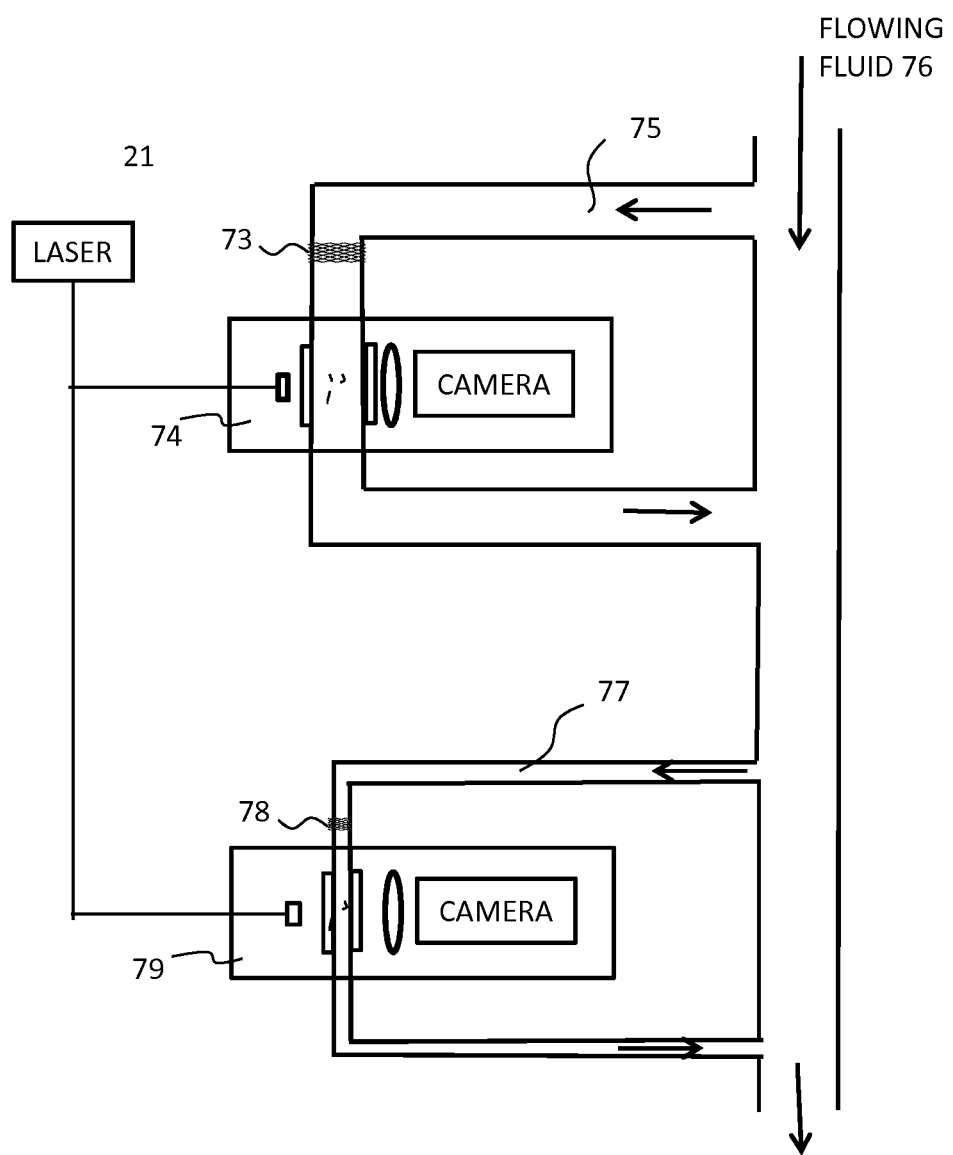
FIG. 7 illustrates an optical particle monitoring system for fluids in which the individual sensor heads/viewing cells are connected separately to the main flow.

FIG. 7 illustrates another example in which the individual sensor heads/viewing cells are connected separately to the main flow line and combined with filters such that the larger particles do not flow through a cell chosen for monitoring smaller particles. In this example, a main fluid flow 76 is tapped at two different locations to provide fluid to conduits 75 and 77. Each conduit includes a filter 73, 78 with a mesh sized to exclude undesirably large particles from the viewing cells in the sensor heads 74 and 79. As discussed above, the viewing window size and filters can be selected to have different sizes to provide a wider particle size imaging capacity or can be sized identically, provide redundant capability. Although two sensor heads 74, 79 are shown in FIG. 7, it is noted that more sensor heads can be included to provide additional capability.

Figure 8:
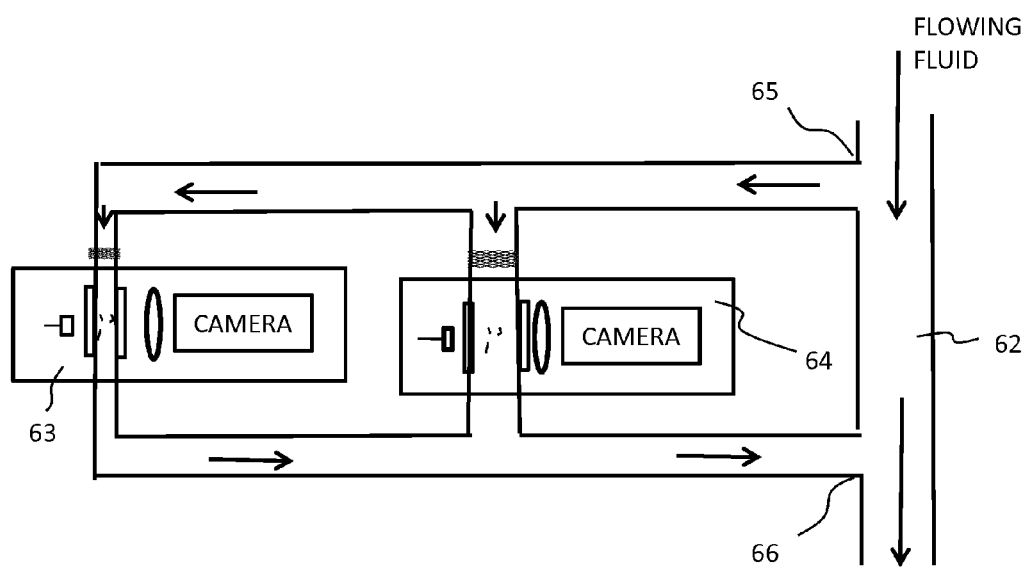
FIG. 8 illustrates an optical particle monitoring system for fluids in which the individual sensor heads/viewing cells are connected in parallel to the main flow.

FIG. 8 shows an exemplary fluid monitoring system in which multiple sensor heads 63, 64 are arranged in parallel conduits having a single tap point 65 and a single return point 66 from the main fluid flow 62. In this example, the viewing cells in the sensor heads are sized to image different particle size ranges. The parallel configuration of FIG. 8 needs less total pressure drop than sensor heads arranged in series. In addition, in the parallel arrangement, if a filter becomes clogged, only the cell in that parallel arm is lost.

It is to be understood that the number of sensor heads can be greater than that the two sensor heads shown in each of FIGS. 7 and 8, depending on the complexity of the system to be monitored and the type and variety of sizes of the particles to be imaged.

It is to be understood that lasers and computer processors, plus any necessary optical and electronic transmission links, are included in the systems shown in FIG. 7 and FIG. 8. The FIG. 7 and FIG. 8 optical fluid monitoring systems can be configured with a single laser coupled to all of the sensor heads or with a laser for each sensor head. Each of the systems can be configured with a single computer processor coupled to all of the sensor heads or with a computer processor for each sensor head.

Figure 9:
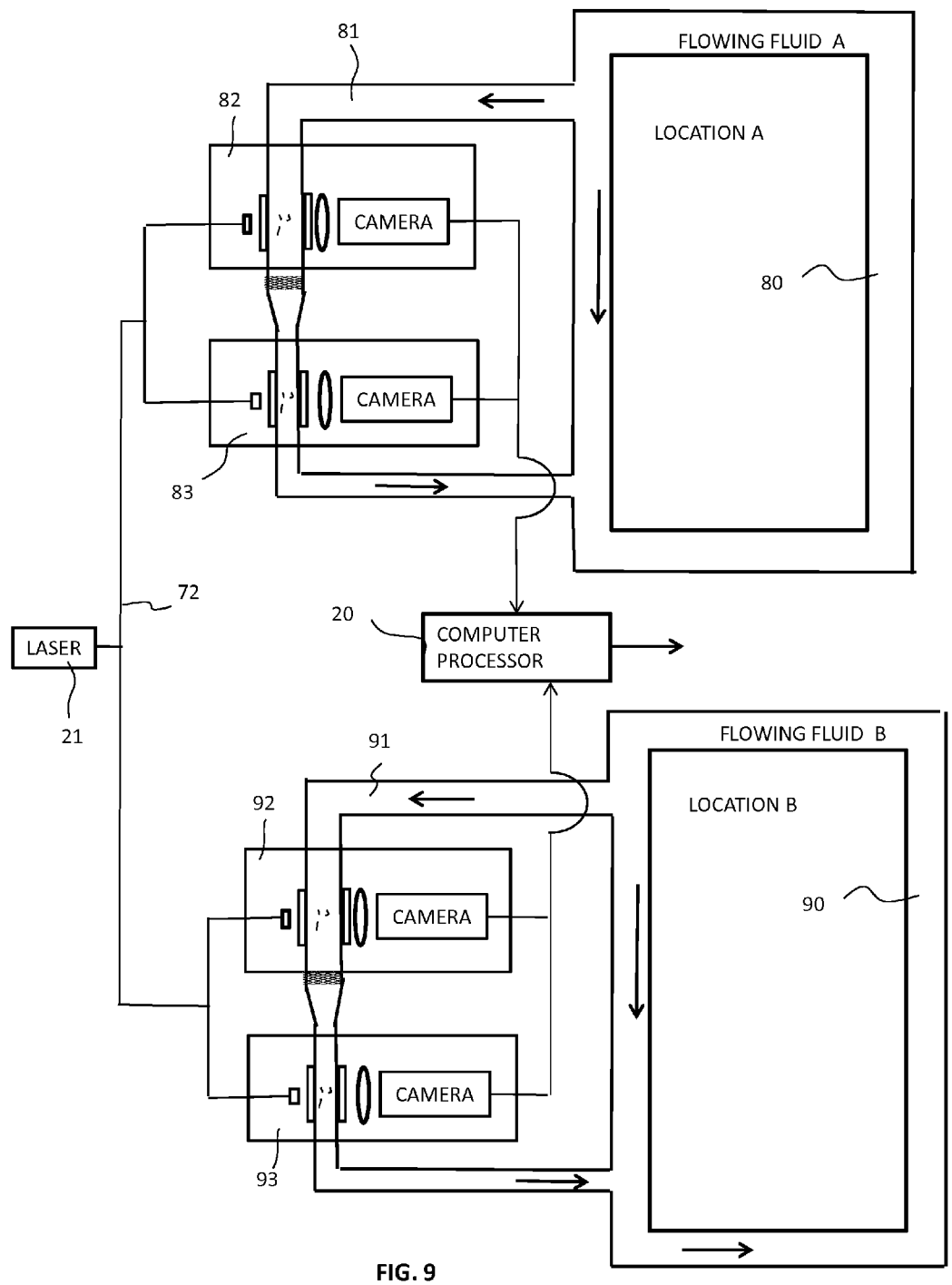
FIG. 9 illustrates an optical particle monitoring system for fluids in which a single laser supplies optical pulses to multiple sensor heads located on several pieces of equipment.

FIG. 9 shows an exemplary fluid monitoring system in which a single laser 21 supplies optical pulses to multiple sensor heads located on several different fluid flow conduits. In this example, a portion of a closed system fluid flow 80 flows into a conduit 81 for particle imaging and analysis. Sensor heads 82 and 82 image the fluid in the conduit in the manner discussed above. The system can include filters and pipe reduction fittings, or the sensor heads 82 and 83 can be redundant systems, similar to the example shown in FIG. 5 and discussed above.

In each of the examples discussed above in which a single laser supplies laser optical energy to a plurality of sensors, the multiplexing of the laser signal for multiple sensors can be accomplished by division of the optical energy from the laser 21 into optical fibers leading to each viewing cell or sensor head. Alternatively, temporal multiplexing can be used, in which an entire pulse is directed to a single one of the cells, with different cells being illuminated in sequence using appropriate switching electronics. For a multiple sensor-head system with temporal multiplexing of return signals, the pulse repetition rate can be set to allow the signals from the sensor heads to be sequentially transmitted.

The systems described herein can advantageously provide information about a broader particle size range than previous near field optical fluid particle monitoring systems. In addition, the systems can provide redundancy in case of equipment failure, particularly for equipment that is difficult or dangerous to access.

Examples of fluids that are suitable for optical monitoring include, but are not limited to, lubricating and power transmission fluids, cooling liquids, water and water mixtures, fuels, and gases.

The systems described herein can also simultaneously monitor the presence of particles in different fluid systems. As one example, a vessel, a station, or a platform can include various pieces of equipment, each of which can have one or more fluids requiring monitoring (e.g., the fluids in the engines, transmission, and bearings on ships, aircraft, oil drilling platforms or other industrial installations such as power generating stations. A single laser illuminator and computer processor can be used to monitor multiple engines, transmission, bearings on ships, aircraft, oil drilling platforms or other industrial installations such as power generating stations.

In several of these examples, components of the system (e.g., laser, computer processor, user control station) can be located remotely from the conduit and the sensor heads. The distance between the laser and the viewing window in the sensor head, for example, can be several kilometers or more, and is limited only by the transmission capability of the optical fiber between the components. Similarly, the computer processor can be several kilometers or more from the imaging system in the sensor head.

In these examples, a notional sampling system, with simple pipe fittings from the main flow passage, has been shown for illustrative purposes. It is to be understood that the sampling systems described in U.S. Pat. No. 6,049,381 to Reintjes et al., U.S. Pat. No. 6,049,381 to Reintjes et al., U.S. Pat. No. 7,921,739 to Fjerdingstad et al., and U.S. Pat. No. 8,056,400 to Reintjes et al., are suitable for use in these systems. These documents are incorporated herein in their entireties.

The invention has been described with reference to certain preferred embodiments. It will be understood, however, that the invention is not limited to the preferred embodiments discussed above, and that modification and variations are possible within the scope of the appended claims.

What is claimed as new and desired to be protected by Letters Patent of the United States is:

1. An optical fluid monitoring system for imaging particles in at least two conduits, each of the conduits arranged in parallel to receive a portion of a flowing fluid from a main flow passageway, the system comprising:
    each of the conduits having an optical sensor positioned to transmit laser optical energy into a transparent viewing window in the conduit in a direction across the direction of flow, each sensor having an optical imaging system for receiving the optical energy after it has passed through the fluid flow and for imaging particles in the fluid flow,
    wherein a first of the plurality of optical sensors is configured to image a range of larger size particles and a second of the plurality of optical sensors is configured to image a range of smaller size particles,
    wherein the first sensor conduit has a conduit thickness that is larger than the second sensor conduit, and
    wherein the conduit thickness at each of the optical sensors is such that the particles in the size range to be imaged are in the optical near field of the corresponding imaging system.

2. The optical fluid monitoring system of claim 1, wherein the parallel conduits connect to a main flow passage at a same tap point and at a same return point.

3. The optical fluid monitoring system of claim 1, further comprising: a filter in at least one of the conduits sized to exclude particles larger than a predetermined size from reaching the optical sensor in that conduit.

4. The optical fluid monitoring system of claim 1, wherein each optical sensor includes a laser.

5. The optical fluid monitoring system of claim 4, wherein the lasers in each optical sensor have different wavelengths.

6. The optical fluid monitoring system of claim 4, wherein each optical sensor includes at least one optical fiber configured to transmit the optical energy of the laser to the transparent viewing window.

7. The optical fluid monitoring system of claim 1, further comprising:
    a single laser operatively coupled to all of the optical sensors.

8. The optical fluid monitoring system of claim 7, further comprising:
    a plurality of optical fibers transmitting the optical energy output of the laser to the transparent viewing windows.

9. The optical fluid monitoring system of claim 1, wherein each imaging system includes a camera and a lens, the lens disposed between the camera and a viewing window in the conduit.

10. The optical fluid monitoring system of claim 1, further comprising:
    a single computer processor operatively connected to receive images from all of the imaging systems, the computer processor having programmed instructions for classifying particle shapes and sizes from the images received from the imaging system.

11. The optical fluid monitoring system of claim 1, wherein each optical sensor includes a computer processor operatively connected to the imaging system in the optical sensor, each of the computer processor having programmed instructions for classifying particle shapes and sizes from the images received from the imaging system.

12. The optical fluid monitoring system of claim 11, wherein the computer processor is located remote from the optical sensors.

13. The optical fluid monitoring system of claim 1, further comprising:
   a single laser operatively coupled to all of the optical sensors; and
   a single computer processor operatively connected to receive images from all of the imaging systems, the computer processor having programmed instructions for classifying particle shapes and sizes from the images received from the imaging system.

14. An optical fluid monitoring system for imaging particles in a flowing fluid, the system comprising:
   at least two flow conduits positioned to receive a portion of a flowing fluid from a main flow passageway and to return the portion of the flowing fluid to the main passageway,
   each of the conduits having an optical sensor positioned to transmit laser optical energy into a transparent viewing window in the conduit in a direction across the direction of flow, each sensor having an optical imaging system for receiving the optical energy after it has passed through the fluid flow and for imaging particles in the fluid flow,
   wherein a first of the plurality of optical sensors is configured to image a range of larger size particles and a second of the plurality of optical sensors is configured to image a range of smaller size particles,
   wherein the first sensor conduit has a conduit thickness that is larger than the second sensor conduit, and
   wherein the conduit thickness at each of the optical sensors is such that the particles in the size range to be imaged are in the optical near field of the corresponding imaging system, and wherein a tap point and a return point for one of the conduits are both positioned downstream of a tap point and a return point for another one of the conduits.

15. The optical fluid monitoring system of claim 14, further comprising: a filter in at least one of the conduits sized to exclude particles larger than a predetermined size from reaching the optical sensor in that conduit.

16. The optical fluid monitoring system of claim 14, wherein each optical sensor includes a laser.

17. The optical fluid monitoring system of claim 16, wherein the lasers in each optical sensor have different wavelengths.

18. The optical fluid monitoring system of claim 14, wherein each optical sensor includes at least one optical fiber configured to transmit the optical energy of the laser to the transparent viewing window.

19. The optical fluid monitoring system of claim 14, further comprising:
   a single laser operatively coupled to all of the optical sensors.

20. The optical fluid monitoring system of claim 19, further comprising:
   a plurality of optical fibers transmitting the optical energy output of the laser to the transparent viewing windows.

21. The optical fluid monitoring system of claim 14, wherein each imaging system includes a camera and a lens, the lens disposed between the camera and a viewing window in the conduit.

22. The optical fluid monitoring system of claim 14, further comprising:
   a single computer processor operatively connected to receive images from all of the imaging systems, the computer processor having programmed instructions for classifying particle shapes and sizes from the images received from the imaging system.

23. The optical fluid monitoring system of claim 14, wherein each optical sensor includes a computer processor operatively connected to the imaging system in the optical sensor, each of the computer processor having programmed instructions for classifying particle shapes and sizes from the images received from the imaging system.

24. The optical fluid monitoring system of claim 23, wherein the computer processor is located remote from the optical sensors.

25. The optical fluid monitoring system of claim 14, further comprising:
   a single laser operatively coupled to all of the optical sensors; and
   a single computer processor operatively connected to receive images from all of the imaging systems, the computer processor having programmed instructions for classifying particle shapes and sizes from the images received from the imaging system.

* * * * *